United States Patent
Kanyilmaz et al.

(10) Patent No.: US 11,579,007 B2
(45) Date of Patent: Feb. 14, 2023

(54) METHOD FOR CALIBRATION OF A DEVICE FOR MEASURING A MASS OF FUEL IN A TANK

(71) Applicant: Airbus Operations SAS, Toulouse (FR)

(72) Inventors: Emre Kanyilmaz, Blagnac (FR); Alvaro Ruiz Gallardo, Toulouse (FR)

(73) Assignee: Airbus Operations SAS, Toulouse (FR)

( * ) Notice: Subject to any disclaimer, the term of this patent is extended or adjusted under 35 U.S.C. 154(b) by 491 days.

(21) Appl. No.: 16/716,706

(22) Filed: Dec. 17, 2019

(65) Prior Publication Data
US 2020/0200585 A1 Jun. 25, 2020

(30) Foreign Application Priority Data
Dec. 19, 2018 (FR) ...................................... 1873408

(51) Int. Cl.
*G01F 23/00* (2022.01)
*G01F 23/292* (2006.01)
(Continued)

(52) U.S. Cl.
CPC .............. *G01F 23/292* (2013.01); *B64F 5/60* (2017.01); *G01K 13/00* (2013.01); *G01N 9/00* (2013.01); *G01N 27/22* (2013.01); *G01N 33/22* (2013.01)

(58) Field of Classification Search
CPC ........ B64D 37/16; B64D 37/32; B64D 37/00; B64D 37/005; G01F 23/22; G01F 1/86;
(Continued)

(56) References Cited

U.S. PATENT DOCUMENTS 4,872,120 A * 10/1989 Orloff .................... B64D 37/00
  73/304 C
4,918,619 A * 4/1990 Orloff ................... G01F 23/263
  73/304 C
(Continued)

FOREIGN PATENT DOCUMENTS

EP 2515090 A1 10/2012

OTHER PUBLICATIONS

French Search Report; priority document.
(Continued)

*Primary Examiner* — Vinh P Nguyen
(74) *Attorney, Agent, or Firm* — Greer, Burns & Crain, Ltd.

(57) ABSTRACT

A method for calibrating a device for measuring a mass of fuel carried by an aircraft by: receiving a message containing a reference permittivity, a reference density and a reference volume, determining a first calibration coefficient as a function of the reference permittivity, determining a second calibration coefficient as a function of the reference volume, determining a third coefficient of calibration as a function of the reference density, determining a calibrated mass of fuel as a function of a determined height of fuel corrected as a function of the first calibration coefficient, a volume of fuel determined as a function of the corrected height and corrected as a function of the second calibration coefficient, and a mass of fuel determined as a function of the corrected volume and corrected as a function of the third calibration coefficient.

9 Claims, 3 Drawing Sheets

(51) Int. Cl.
*B64F 5/60* (2017.01)
*G01K 13/00* (2021.01)
*G01N 9/00* (2006.01)
*G01N 27/22* (2006.01)
*G01N 33/22* (2006.01)

(58) Field of Classification Search
CPC .......... G01F 22/00; G01F 23/292; G01F 1/00; G01F 23/80; G01F 25/10; G01F 25/20; G01F 1/07; G01F 23/268; G01F 23/263; G01F 23/266; G01N 33/22; G01N 27/22; G01N 9/00; G01N 27/221; G01N 33/225; G01N 21/85; G01N 2291/02818; G01N 2291/02836; G01N 9/002; G01N 2027/222; G01N 27/226; B64F 5/60; G06K 9/6263; G06K 9/6251; B64C 17/10; G05B 19/0425; G05B 19/0426; G05B 2219/33331; G05B 23/02; G01K 13/00; G01G 9/00; G01G 19/09; F02C 7/22; F02C 9/26
See application file for complete search history.

(56) References Cited

U.S. PATENT DOCUMENTS

| | | | | |
|---|---|---|---|---|
| 5,138,559 | A * | 8/1992 | Kuehl | G01F 23/804 |
| | | | | 73/292 |
| 5,265,460 | A * | 11/1993 | Ellinger | G01N 9/00 |
| | | | | 73/32 R |
| 6,157,894 | A * | 12/2000 | Hess | G01F 23/18 |
| | | | | 702/50 |
| 8,515,694 | B1 * | 8/2013 | Orloff | G01F 23/804 |
| | | | | 73/1.72 |
| 8,677,819 | B2 * | 3/2014 | Austerlitz | B64D 37/005 |
| | | | | 73/304 C |
| 9,909,967 | B2 * | 3/2018 | McBrien | G01F 25/10 |
| 10,041,879 | B2 * | 8/2018 | Zakrzewski | G01F 22/00 |
| 10,442,545 | B2 * | 10/2019 | Crowne | B64D 37/04 |
| 10,627,280 | B2 * | 4/2020 | Zakrzewski | G01F 23/804 |
| 2012/0260731 | A1 | 10/2012 | Austerlitz et al. | |

OTHER PUBLICATIONS

T. Ford, "On-Board Refuelling Systems Development," Aircraft Engineering and Aerospace Technology, Emerald Group Publishing, Bradford, GB, vol. 68, No. 5, Jan. 1, 1996, pp. 15-20.

* cited by examiner (prior art)

METHOD FOR CALIBRATION OF A DEVICE FOR MEASURING A MASS OF FUEL IN A TANK

CROSS-REFERENCES TO RELATED APPLICATIONS

This application claims the benefit of the French patent application No. 1873408 filed on Dec. 19, 2018, the entire disclosures of which are incorporated herein by way of reference.

FIELD OF THE INVENTION

The present invention concerns the field of aircraft onboard systems. The invention more particularly concerns a device for measurement of a mass of fuel in a tank of the aircraft and a method for calibration of said device.

BACKGROUND OF THE INVENTION

An aircraft includes at least one tank adapted to contain a fuel necessary for the operation of its engines. These tanks are frequently situated in the wings of the aircraft, which wings are then, at least in part, hollow. It is essential that the crew flying the aircraft have at all times a measurement of the quantity of fuel remaining in the tanks of the aircraft. This quantity is typically expressed as a mass of fuel contained in the tanks and is determined by an appropriate measuring device integrated into the avionics system of the aircraft.

The determination of the quantity of fuel present in the tanks by the measuring device onboard the aircraft must be as accurate as possible. The accuracy required for this kind of onboard measuring device is typically of the order of plus or minus one percent (+/−1%). For an aircraft carrying tens of tons of fuel this may represent a margin of error of the order of several hundred kilograms of fuel. Thus, if the measuring device built into the aircraft underestimates the mass of fuel carried by several hundred kilograms, that represents a significant loss of operation throughout the operating service life of the aircraft.

It is therefore necessary to propose a method for calibration of a device for measurement of a mass of fuel in a tank of an aircraft enabling this disadvantage to be alleviated.

SUMMARY OF THE INVENTION

The invention concerns a method for calibration of a device for measuring a mass of fuel contained in a tank of an aircraft, the measuring device comprising:
  at least one probe adapted to measure a parameter enabling determination of the mass of fuel contained in the tank,
  the measuring device being adapted:
  to determine a mass of fuel contained in the tank as a function of at least one parameter measured by at least the probe,
  the calibration method being executed by the device during an operation of filling the tank and being characterized in that it comprises the steps of:
  receiving at least one message comprising at least one calibration datum,
  determining at least one calibration coefficient for the measurements effected by at least the probe as a function of the calibration datum received and the measured mass of fuel,
  determining a calibrated mass of fuel contained in the tank as a function at least of the calibration coefficient.

In accordance with a complementary embodiment of the invention the measuring device comprises:
  a probe for measuring the dielectric permittivity of the fuel,
  a probe for measuring the density of the fuel,
  at least one probe for measuring the capacitance of the fuel,
  the measuring device being adapted, to determine a mass of fuel contained in the tank as a function of the parameters measured by the probes:
    to determine at least one height of the fuel contained in the tank as a function at least of the measured permittivity, temperature and capacitance of the fuel,
    to determine a volume of fuel contained in the tank as a function of the height of fuel previously determined and a 3D model of the tank,
    to determine the mass of fuel contained in the tank as a function of the volume previously determined and the measured density of the fuel,
  the calibration data comprising a reference permittivity of the fuel, a reference density of the fuel, a reference capacitance and a volume of fuel placed in the tank,
  to determine as a function of the received calibration datum and the measured mass of fuel at least one calibration coefficient for the measurements effected by at least the probe comprising:
    determining a first calibration coefficient as a function of the permittivity of the fuel measured by the device and the reference permittivity,
    determining a second calibration coefficient as a function of the volume of fuel determined by the device and the volume of fuel placed in the tank,
    determining a third calibration coefficient as a function of the density of the fuel measured by the device and the reference density,
    determining a calibrated mass of fuel contained in the reservoir being as a function of:
      the determined height of fuel corrected as a function of the first calibration coefficient,
      the volume of fuel determined as a function of the corrected height and corrected as a function of the second calibration coefficient, and
      the mass of fuel determined as a function of the corrected volume and corrected as a function of the third calibration coefficient.

In accordance with a complementary embodiment of the invention, the calibration datum comprises a datum emanating from a probe of a filling system adapted to measure the parameter enabling determination of the mass of the fuel contained in the tank.

In accordance with a complementary embodiment of the invention, the calibration datum comprises a mass of fuel placed in the tank during an operation of filling the tank.

The invention also concerns a device for measuring a mass of fuel contained in a tank of an aircraft, the measuring device comprising:
  at least one probe adapted to measure a parameter enabling determination of the mass of fuel contained in the tank,
  the measuring device being adapted:
  to determine a mass of fuel contained in the tank as a function of the parameter measured by the probe,
  and, during an operation of filling the tank:
  receiving at least one message comprising at least one calibration datum, determining at least one calibration coefficient for the measurements effected by the probe as a function of the calibration datum received and the measured mass of fuel, determining a calibrated mass of fuel contained in the tank as a function at least of the calibration coefficient.

In accordance with a complementary embodiment of the invention the measuring device comprises:

a probe for measuring the dielectric permittivity of the fuel, a probe for measuring the density of the fuel, at least one probe for measuring the capacitance of the fuel, the measuring device being adapted:

to determine a height of the fuel contained in the tank as a function at least of the measured permittivity of the fuel, to determine a volume of fuel contained in the tank as a function of the height of fuel previously determined and a 3D model of the tank, to determine the mass of fuel contained in the tank as a function of the volume previously determined and the measured density of the fuel, the device being adapted to execute the calibration method according to the invention.

In accordance with a complementary embodiment of the invention, the device comprises a display module adapted to display:

the mass determined before calibration, and/or the mass determined after calibration, and an alert if the difference between the mass determined before and after calibration is above a predetermined threshold.

In accordance with a complementary embodiment of the invention, the measuring device comprises a communication module adapted to receive at least one calibration datum.

In accordance with a complementary embodiment of the invention, the measuring device comprises a communication module adapted to receive at least one message containing a reference permittivity of the fuel, a reference density of the fuel and a volume of fuel placed in the tank.

The invention also concerns a computer program characterized in that it comprises instructions for execution by a processor of a device for measuring a mass of fuel contained in a tank of an aircraft of a calibration method according to the invention when the computer program is executed by the processor. The invention also concerns a storage medium readable by a device for measuring a mass of fuel contained in a tank of an aircraft on which said computer program is stored.

BRIEF DESCRIPTION OF THE DRAWINGS

The features of the invention mentioned hereinabove and others will become more clearly apparent on reading the following description of one embodiment, said description being given with reference to the appended drawings, in which.

DETAILED DESCRIPTION OF THE PREFERRED EMBODIMENTS

Today, ground fueling systems—fuel pumps—intended to fill the tanks of an aircraft are able to measure the mass and/or the volume of fuel supplied to an aircraft with a margin of error much narrower than that made possible by a device onboard an aircraft. The accuracy of the measurement of the fuel supplied can therefore be of the order of 0.05%, which is twenty times greater than the accuracy of a device onboard an aircraft. It is then judicious to use that accuracy in order to be able to calibrate the onboard measuring device during a phase of filling the tanks of an aircraft, which is an object of the present invention. The accuracy of the measurements offered by the onboard device can then be improved once the calibration has been effected.

Figure 1:
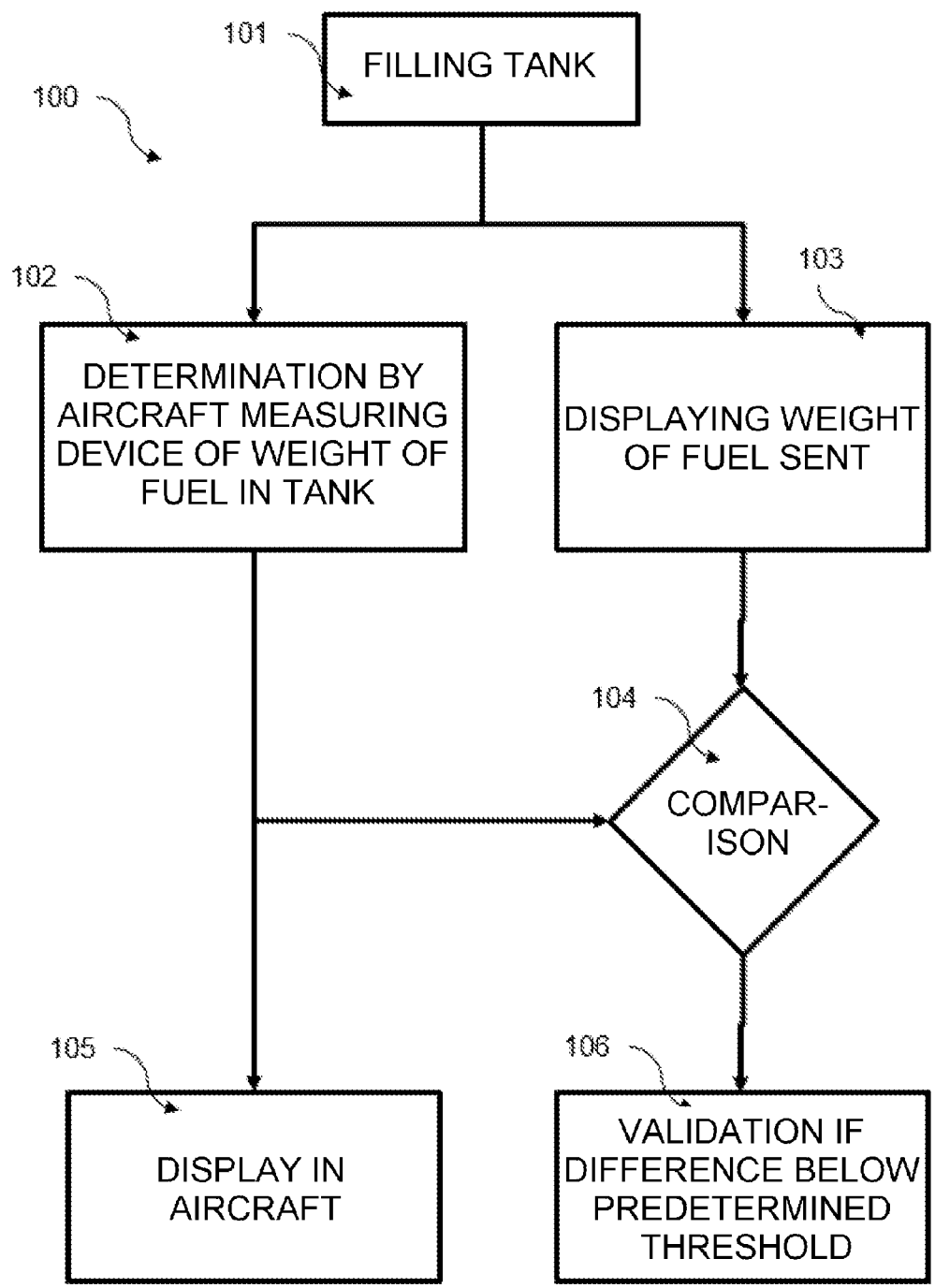
FIG. 1 is a diagram representing a method for validation of a measurement of a mass of fuel in a tank of an aircraft in accordance with an embodiment known to the person skilled in the art.

FIG. 1 is a diagram showing a method 100 of validating a measurement of a mass of fuel in a tank of an aircraft in accordance with an embodiment known to the person skilled in the art.

In a first step 101 a ground fueling system—or fuel pump—fills the tanks of the aircraft. The fueling system hypothetically comprises probes for measuring the volume and the mass of fuel fed to the tanks enabling a greater measurement accuracy than the accuracy provided by the measuring device onboard the aircraft.

Either empty tanks or previously drained tanks are filled.

In a step 102 the onboard measuring device determines a mass of fuel contained in the tanks using a method known to the person skilled in the art.

Thus, a measuring device may typically comprise:

a probe for measuring the dielectric permittivity of the fuel contained in the tanks, a probe for measuring the density of the fuel contained in the tanks, a probe for measuring the temperature of the fuel contained in the tanks, a plurality of probes adapted to measure a height of fuel as a function of a measured capacitance, these probes being disposed in the tanks.

The measuring device is therefore adapted to measure a temperature, a dielectric permittivity (hereinafter permittivity) and a density of the fuel contained in the tanks.

The method for determining the mass of fuel contained in the tanks typically comprises three steps executed by the measuring device:

1) determination of a height of fuel for each probe, each height measured for a probe being a function of a capacitance measured by the probe, of the temperature of the fuel and of the permittivity of the fuel, 2) determination of a volume of fuel contained in a tank, the measured volume being a function of the heights previously measured and a three-dimensional model of the tank, 3) determination of the mass of fuel, the measured mass of fuel being a function of the volume previously measured and the density of the fuel.

This method therefore enables measurement of the mass of fuel contained in a tank in three steps, each step being dependent on the preceding step, as a function of:

the permittivity of the fuel measured by a probe of the measuring device, the temperature of the fuel measured by a probe of the measuring device, the density of the fuel measured by a probe of the measuring device, measurement of a capacitance for each probe of the measuring device placed in the tanks, a three-dimensional model of each tank enabling determination of a volume of fuel as a function in particular of the height of fuel measured by the probes.

The onboard measuring device is therefore autonomously able to measure the mass of fuel contained in the tanks.

Once the tank or tanks have been filled or while filling it or them, in a step 103, the ground fueling system displays or sends to a control device the mass of fuel supplied during fueling.

In a step 104, the mass of fuel as measured by the onboard measuring device is compared with the mass of fuel as measured by the fueling system.

If the difference between the two measured masses of fuel is below a predetermined threshold, for example an absolute value of plus or minus one percent (+/−1%) then, in a step 106, the filling of the tanks and the display of the correct mass of fuel by the onboard measuring device is validated.

In this case, in a step 105, the display of the mass of fuel by the measuring device is validated, this measured value being displayable and usable by a crew of the aircraft.

It is to be noted that the process described in step 102 is repeated periodically in order to update the mass of fuel remaining in the tanks during use of the aircraft.

Figure 2:
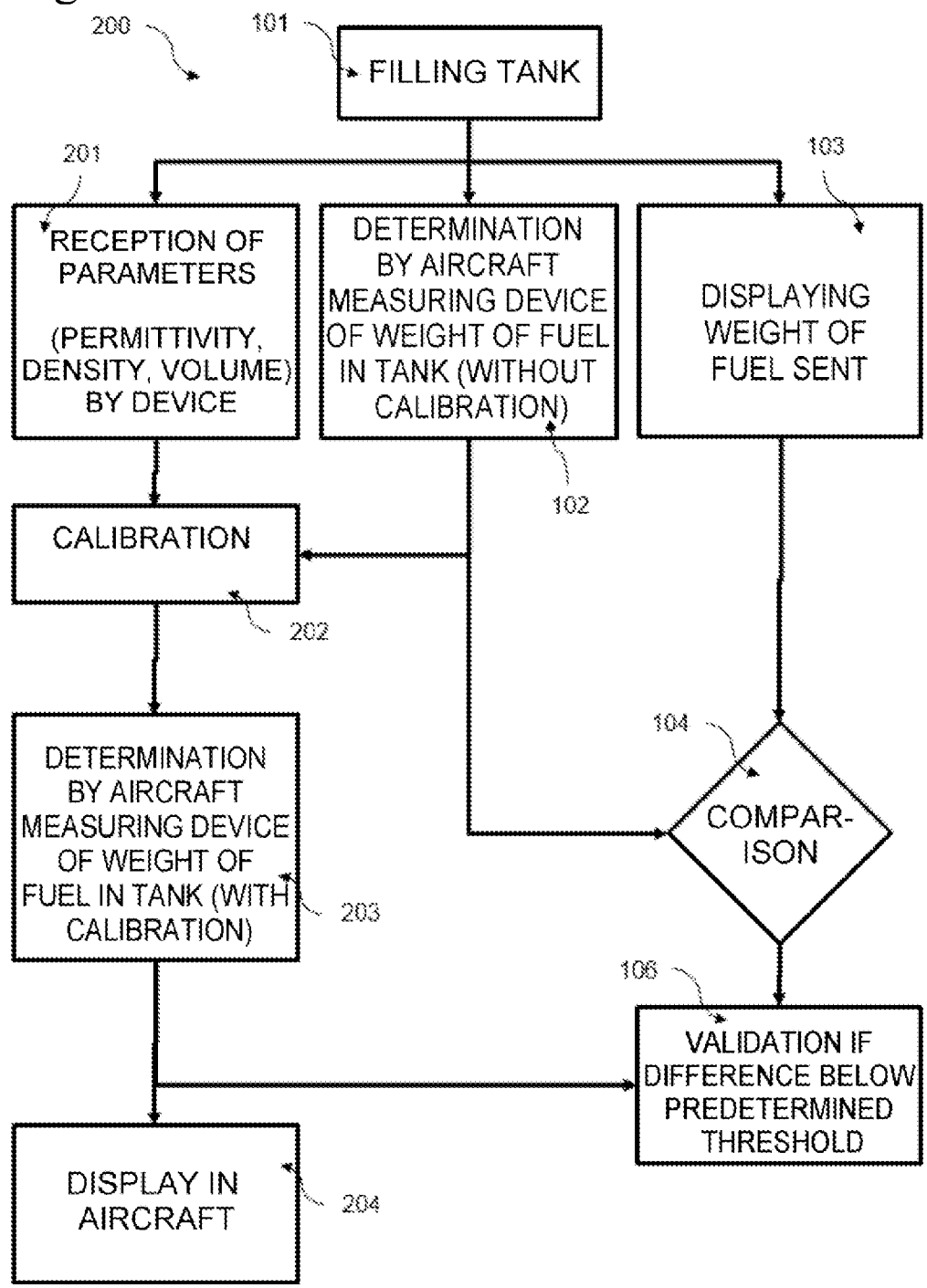
FIG. 2 is a diagram representing a method for calibration of a device for measurement of a mass of fuel in a tank of an aircraft in accordance with one embodiment of the invention.

FIG. 2 is a diagram showing a method 200 for calibration of a device for measuring a mass of fuel in a tank of an aircraft in accordance with one embodiment of the invention.

In a similar manner to the method 100, either empty tanks or previously drained tanks are filled.

As for the method 100, during the steps 101 and 103 the fueling system feeds fuel to the tanks of the aircraft and measures the quantity of fuel supplied. This quantity may be displayed or sent to a control device.

The method 200 differs in that, in a step 201, the fueling system or any other control device connected to the fueling system sends the onboard measuring device in the aircraft one or more messages comprising one or more calibration data items such as, for example, a reference permittivity of the fuel, a reference density of the fuel and a volume of fuel placed in the tank. The reference permittivity of the fuel and the reference density of the fuel are typically measurements of the permittivity and the density of the fuel effected, for example, by probes of the fueling system, these measurements being hypothetically more accurate than those made possible by the probes of the onboard measuring device. Similarly, a precise measurement—that is to say, one with the accuracy made possible by the fueling system, better than that of the onboard measuring device—is sent to the onboard measuring device. The onboard measuring device is therefore adapted to receive at least one message comprising a reference permittivity of the fuel, a reference density of the fuel and a volume of fuel placed in the tank (or reference volume).

The measuring device is adapted, on the basis of the data received in the step 201:

to determine a first calibration coefficient as a function of the permittivity of the fuel measured by the device and the reference permittivity, to determine a second calibration coefficient as a function of the volume of fuel determined by the device and the volume of fuel placed in the tank (or reference volume), to determine a third calibration coefficient as a function of the density of the fuel measured by the device and the reference density.

The first calibration coefficient therefore enables correction of the height value of fuel measured by a probe. A first height value is conventionally determined as a function of a capacitance measured by the probe, of the temperature of the fuel and of the permittivity of the fuel, the temperature and the permittivity being measured by the measuring device. A second height value for the same probe is determined using, instead of the permittivity supplied by the measuring device, the reference permittivity received in a message. The first calibration coefficient is then a coefficient making it possible to change from the first height value to the second height value. The measuring device is then able to execute the method for determination of the mass of fuel contained in the tanks as described above in step 102, correcting each measurement of height of fuel by a probe using a first calibration coefficient. Each probe is associated with its own first calibration coefficient.

Any offset in the positioning of each probe can therefore be corrected if, for example, a probe is moved a few millimeters up or down.

More generally, receiving an intermediate datum and comparing it to an internal measurement makes it possible to detect a possible malfunction of an internal probe of the device of the aircraft. In other words, the measuring device is able to receive a calibration datum corresponding to a measurement by a probe of an external system, hypothetically more reliable and more accurate, for example, a fueling system. The probe of the fueling system measures the same parameter as the probe of the measuring device in the aircraft. A comparison of the measured values emanating from these two probes—internal and external—enables detection, in the event of inconsistency between the two measurements, of a possible malfunction of the probe of the measuring device.

Similarly, a volume of fuel is determined by the onboard measuring device, this volume being a function of the heights measured by each probe—modified by the first calibration coefficient—and of a three-dimensional model of the tank. This volume determined by the onboard measuring device is compared to the reference volume received in step 201. The second calibration coefficient makes it possible to correct the volume determined by the measuring device in order to obtain the reference volume. A measuring device is then able to execute the method for determination of the mass of fuel contained in the tanks as described above in step 102, correcting each determination of the volume using the second calibration coefficient.

Finally, a first mass of fuel is determined by the onboard measuring device as a function of the volume of fuel previously determined, corrected by the second calibration coefficient, and the density measured by the measuring device. A second mass of fuel is determined by the onboard measuring device as a function of the volume of fuel determined previously, corrected by the second calibration coefficient, and the reference density received in step 201. The third calibration coefficient makes it possible to correct the first value of the mass in order to obtain the second value of mass of fuel. This second value of the mass of fuel is equal to the mass of fuel supplied by the fueling system. The measuring device is then able to execute the method for determination of the mass of fuel contained in the tanks as described above in step 102, correcting each determination of the mass of fuel using the third calibration coefficient.

Thus, any inaccuracy in the measurement of the density of the fuel by the onboard measuring device can be corrected.

In a manner similar to the method 100, the filling and the display of the correct mass of fuel onboard is validated as a function of the mass of fuel determined without calibration.

In contrast, in a step 204 it is the mass of fuel determined with calibration that is displayed for use by the crew of the aircraft.

In accordance with one embodiment of the invention the onboard measuring system is adapted to display:

the mass of fuel determined with and/or without calibration, whichever is the greater of the mass determined with calibration and the mass determined without calibration, or whichever is the lower of the mass determined with calibration and the mass determined without calibration, or the value of the mass of fuel determined with calibration provided that the difference with respect to the mass of fuel determined without calibration is below a predetermined threshold, for example 1%, and the mass determined without calibration otherwise, an alert if the difference between the determined mass, for example 1%, before and after calibration is above a predetermined threshold.

In accordance with an alternative embodiment of the invention, the method 200 may more generally comprise the following alternative steps executed by the measuring device:

a step 201 of receiving a message emanating from the fueling system, the message comprising at least one datum enabling calibration of the measurements effected by the measuring device, a step 202 of calibration as a function of the datum or data previously received.

In accordance with a complementary or alternative embodiment of the invention, the measuring device may comprise probes of different types, according to the method employed to determine a mass of fuel in the tank based on the measurements from said probes. For example, the measuring device may alternatively or additionally comprise probes enabling measurement of a pressure, an optical probe, comprising a LASER for example, enabling measurement of a height between the surface of the fuel present in the tank and the top of the tank, a probe for measurement of a temperature of the air in the tank, etc.

It is to be noted that the ground fueling system and the onboard measuring device in the aircraft can use different measuring methods. However, the fueling system may be adapted to supply to the onboard measuring device the data necessary for calibration of the measuring device.

The method 200 may therefore comprise a step before the step 201 of exchange of information between the fueling system and the measuring device, the measuring device, for example, informing the fueling system of the measuring method employed or the necessary calibration information.

Alternatively, the method may comprise a step before step 201 in which the fueling system informs the measuring device of data that the fueling system is able to supply to the measuring device, the measuring device then being able to select the data necessary for a calibration operation. The measuring device may possibly employ a different calibration method depending on the data available from the fueling system.

In accordance with one embodiment of the invention the fueling system supplies to the measuring device in step 201 a datum corresponding to the mass of fuel fed into the tank. The measuring device is then able to execute the calibration step by comparing the mass given by its own measurement and the mass given by the fueling system, a calibration correct coefficient then being calculated. This coefficient may be a multiplier type coefficient corresponding, for example, to the ratio between the two values, the mass given by the measuring device's measurement being multiplied by this coefficient in order to obtain a corrected mass. This coefficient may also consist in a so-called calibration mass that is then added to or subtracted from the mass measured by the measuring device.

In accordance with a complementary embodiment of the invention the calibration method 200 may be carried out continuously during a fueling operation, the measuring device being able to receive continuously or periodically the mass of fuel actually fed into the tank, calibration then being effected each time. In time, the measurement device is able to determine a global calibration coefficient as a function of various determined calibration coefficients (for example by averaging them) or to determine a calibration coefficient valid for each range of values of the measured mass.

Figure 3:
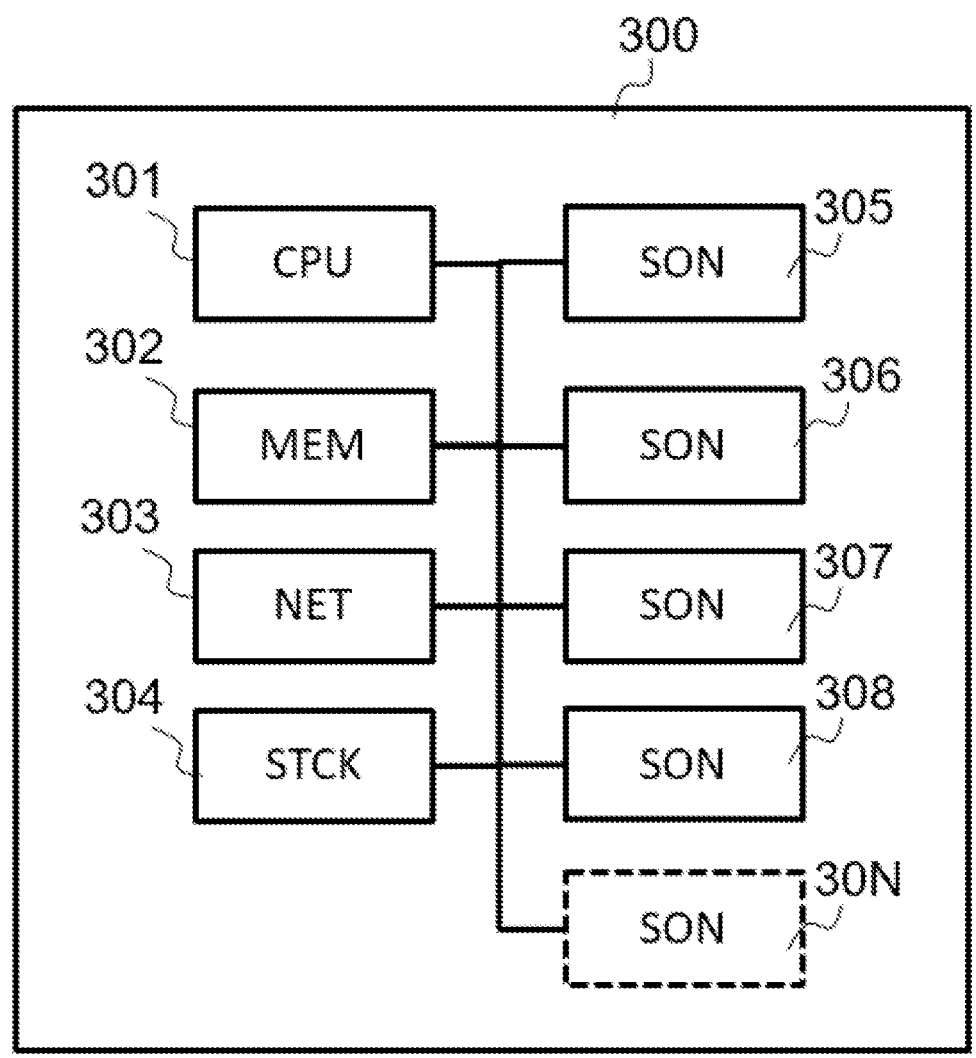
FIG. 3 is a diagram representing an architecture of a device for measuring a mass of fuel in a tank of an aircraft in accordance with one embodiment of the invention.

FIG. 3 is a diagram showing the hardware architecture of a device 300 for measuring a mass of fuel contained in a tank of an aircraft, the device 300 being adapted to execute some or all of the steps of the method 200 shown in FIG. 2.

Thus the device 300 comprises, connected by a communication bus: a central processor unit ((CPU)) 301; a random access memory (RAM) type memory 302 and/or a read only memory (ROM) type memory, possibly a communication module (NET) 303, a storage module (STCK) 304 of internal storage type, a probe (SON) 305 for measuring a temperature, enabling measurement of the temperature of the onboard fuel, a probe (SON) 306 for measuring a dielectric permittivity, enabling measurement of the permittivity of the onboard fuel, a probe (SON) 307 for measuring a density, enabling measurement of the density of the onboard fuel, and possibly a plurality of probes (SON) 308 to 30N enabling measurement of a height of fuel by measurement of a capacitance. For example, the measuring device 300 comprises three probes (SON) 308, 30N for measurement of capacitance in order to measure a height, three height measurements enabling definition of a plane representing the surface of the fuel in the tank. The storage module (STCK) 304 may be of the hard disk drive (HDD) type or solid-state drive (SSD) type, or of external storage medium reader type, such as an SD (Secure Digital) card reader. The communication module 303 may be of AFDX® (Avionics Full DupleX switched Ethernet) type, of ARINC 429 type (standard developed and administered by the Airlines Electronic Engineering Committee (AEEC), a committee of the company ARINC), of CAN (Controller Area Network) type, of FOMAX (Flight Operations and Maintenance eXchanger) type, or of any other type enabling exchange of data between the device 300 and another device, for example a ground fueling system. The processor (CPU) 301 is able to store data or information in the memory MEM 302 or in the storage module (STCK) 304. The processor (CPU) 301 is able to read data stored in the memory MEM 302 or in the storage module (STCK) 304. This data may correspond to configuration parameters. The communication module (NET) 303 typically enables connection of the device 300 to a fueling system or to a local area network and/or the Internet. Each probe (SON) 308 to 30N enables measurement of a height of fuel in a tank as a function in particular of a measure capacitance.

The processor (CPU) 301 is capable of executing instructions loaded into the memory MEM 302, for example from the storage module (STCK) 304. When the device 300 is powered up the processor (CPU) 301 is capable of reading instructions in the memory MEM 302 and executing them. These instructions form a computer program causing execution by the processor (CPU) 301 of some or all of the methods and steps described hereinabove, in particular, the method shown in FIG. 2. Thus, some or all of the methods and steps described hereinabove may be implemented in software by execution of a set of instructions by a programmable machine such as a DSP (Digital Signal Processor) or a microcontroller. Some or all of the methods and steps described here may also be implemented in hardware by a dedicated component or machine such as an FPGA (Field-Programmable Gate Array) or an ASIC (Application-Specific Integrated Circuit). The functions of the device 300 may be integrated into an onboard measuring device by updating software, that is to say for example by updating the firmware of the device 300.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

The invention claimed is:

1. A method for calibration of a measuring device for measuring a mass of fuel contained in a tank of an aircraft, the measuring device comprising:
at least one probe configured to measure a parameter enabling determination of the mass of fuel contained in the tank,
the measuring device being configured:
to determine the mass of fuel contained in the tank as a function of the parameter measured by the at least one probe,
the calibration method being executed by the measuring device during an operation of filling the tank and comprising the steps of:
receiving at least one message comprising at least one calibration datum corresponding to a measurement,
determining at least one calibration coefficient for measurements effected by the at least one probe as a function of the calibration datum received and a measured mass of fuel,
determining a calibrated mass of fuel contained in the tank as a function at least of the calibration coefficient.

2. The method according to claim 1, wherein the at least one probe comprises:
a probe configured to measure, as a parameter, a dielectric permittivity of the fuel,
a probe configured to measure, as a parameter, a density of the fuel,
a probe configured to measure, as a parameter, a capacitance of the fuel, and
a probe configured to measure, as a parameter, a temperature of the fuel,
the measuring device being configured to determine a mass of fuel contained in the tank as a function of the parameters measured by the probes:
to determine at least one height of the fuel contained in the tank as a function at least of the measured permittivity, temperature and capacitance of the fuel,
to determine a volume of fuel contained in the tank as a function of both the height of fuel previously determined and a 3D model of the tank,
to determine the mass of fuel contained in the tank as a function of the volume previously determined and the measured density of the fuel,
the at least one calibration datum comprising a reference permittivity of the fuel, a reference density of the fuel and a volume of fuel placed in the tank,
to determine as a function of the received calibration datum and the measured mass of fuel at least one calibration coefficient for the measurements effected by at least the probe comprising:
determining a first calibration coefficient as a function of the permittivity of the fuel measured by the device and of the reference permittivity,
determining a second calibration coefficient as a function of the volume of fuel determined by the device and the volume of fuel placed in the tank,
determining a third calibration coefficient as a function of the density of the fuel measured by the device and the reference density,
determining a calibrated mass of fuel contained in the reservoir being as a function of:
the determined height of fuel corrected as a function of the first calibration coefficient,
the volume of fuel determined as a function of the corrected height and corrected as a function of the second calibration coefficient, and
the mass of fuel determined as a function of the corrected volume and corrected as a function of the third calibration coefficient.

3. The method according to claim 1, wherein the calibration datum comprises the mass of fuel placed in the tank during the operation of filling the tank.

4. A non-transitory computer readable medium comprises a non-transitory computer program when executed by a processor of a device configured to measure a mass of fuel contained in a tank of an aircraft of a calibration method according to claim 1 when the computer program is executed by the processor.

5. A measuring device for measuring a mass of fuel contained in a tank of an aircraft, the measuring device comprising:
at least one probe configured to measure a parameter enabling determination of the mass of fuel contained in the tank,
the measuring device being configured:
to determine the mass of fuel contained in the tank as a function of the parameter measured by the at least one probe,
and, during an operation of filling the tank:
receiving at least one message comprising at least one calibration datum corresponding to a measurement,
determining at least one calibration coefficient for measurements effected by the at least one probe as a function of the calibration datum received and the determined mass of fuel, determining a calibrated mass of fuel contained in the tank as a function at least of the calibration coefficient.

6. The measuring device according to claim 5, further comprising a communication module configured to receive the at least one calibration datum.

7. The measuring device according to claim 5, further comprising a communication module configured to receive at least one message containing a reference permittivity of the fuel, a reference density of the fuel and a volume of fuel placed in the tank.

8. A measuring device for measuring a mass of fuel contained in a tank of an aircraft, the measuring device comprising:
- a probe for measuring, as a parameter, a dielectric permittivity of the fuel,
- a probe for measuring, as a parameter, a density of the fuel,
- at least one probe configured to measure, as a parameter, a capacitance of the fuel,
- a probe configured to measure, as a parameter, a temperature of the fuel,
- the device for measuring the mass of fuel being configured:
  - to determine a height of the fuel contained in the tank as a function at least of the measured permittivity, temperature and capacitance of the fuel,
  - to determine a volume of fuel contained in the tank as a function of both the height of fuel previously determined and a 3D model of the tank,
  - to determine the mass of fuel contained in the tank as a function of the volume previously determined and the measured density of the fuel,
- the device being configured to
  - receive at least one message comprising at least one calibration datum corresponding to a measurement,
  - determining at least one calibration coefficient for measurements effected by the at least one probe as a function of the calibration datum received and a measured mass of fuel, and,
  - determining a calibrated mass of fuel contained in the tank as a function at least of the calibration coefficient.

9. The measuring device according to claim 8, further comprising a display module and being configured to display at least one of:
- the mass determined before calibration, or
- the mass determined after calibration, and
- an alert if a difference between the mass determined before and after calibration is above a predetermined threshold.

* * * * *